(12) United States Patent
Tiefenbach et al.

(10) Patent No.: US 10,539,492 B2
(45) Date of Patent: Jan. 21, 2020

(54) SENSOR FOR DETERMINING A CONCENTRATION OF PARTICLES IN A GAS FLOW

(71) Applicant: Robert Bosch GmbH, Stuttgart (DE)

(72) Inventors: Andy Tiefenbach, Vaihingen-Horrheim (DE); Enno Baars, Leonberg (DE); Sebastian Fuchs, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 58 days.

(21) Appl. No.: 15/517,142

(22) PCT Filed: Aug. 17, 2015

(86) PCT No.: PCT/EP2015/068822
§ 371 (c)(1),
(2) Date: Apr. 5, 2017

(87) PCT Pub. No.: WO2016/058732
PCT Pub. Date: Apr. 21, 2016

(65) Prior Publication Data
US 2017/0307499 A1 Oct. 26, 2017

(30) Foreign Application Priority Data
Oct. 14, 2014 (DE) ......................... 10 2014 220 791

(51) Int. Cl.
*G01N 15/06* (2006.01)
*G01M 15/10* (2006.01)

(52) U.S. Cl.
CPC ...... *G01N 15/0656* (2013.01); *G01M 15/102* (2013.01)

(58) Field of Classification Search
CPC .................... G01N 15/0656; G01M 15/102
See application file for complete search history.

(56) References Cited

U.S. PATENT DOCUMENTS

| | | | |
|---|---|---|---|
| 7,143,637 | B1 | 12/2006 | McBrearty et al. |
| 2008/0024111 | A1 | 1/2008 | Dorfmueller et al. |

(Continued)

FOREIGN PATENT DOCUMENTS

| | | |
|---|---|---|
| CN | 101387614 A | 3/2009 |
| DE | 102004059650 A1 | 6/2006 |

(Continued)

OTHER PUBLICATIONS

International Search Report dated Dec. 7, 2015 of the corresponding International Application PCT/EP2015/068822 filed Aug. 17, 2015.

*Primary Examiner* — Patrick Assouad
*Assistant Examiner* — Feba Pothen
(74) *Attorney, Agent, or Firm* — Norton Rose Fulbright US LLP; Gerard Messina

(57) ABSTRACT

A device for determining a concentration of particles in a gas flow, e.g., soot particles in exhaust gas of an internal combustion engine, includes a carrier and a sensor, which is situated on a surface of the carrier and can be exposed to the gas flow, the sensor including an electrode structure including at least two measuring electrodes that are of different polarity and that are formed as an interdigital comb structure including finger electrodes. In first areas of the interdigital comb structure, the finger electrodes have a first mutual distance in relation to each other, and in second areas of the interdigital comb structure, the finger electrodes have a second smaller mutual distance in relation to each other, the first areas and the second areas in the interdigital comb structure each at least partially adjoining each other alternately, occupying respective surface areas on the sensor.

16 Claims, 14 Drawing Sheets

(56) References Cited

U.S. PATENT DOCUMENTS

2011/0259079 A1\* 10/2011 Maeda ............... G01N 15/0656
73/23.33
2012/0047993 A1\* 3/2012 Tokuda .............. G01N 15/0656
73/23.33
2012/0151992 A1\* 6/2012 Harada .............. G01N 15/0656
73/23.33

FOREIGN PATENT DOCUMENTS

DE 102006029215 A1 1/2008
DE 102006032741 A1 1/2008
JP 2012013639 A 1/2012

\* cited by examiner

SENSOR FOR DETERMINING A CONCENTRATION OF PARTICLES IN A GAS FLOW

CROSS-REFERENCE TO RELATED APPLICATIONS

The present application is the national stage of International Pat. App. No. PCT/EP2015/068822 filed Aug. 17, 2015, and claims priority under 35 U.S.C. § 119 to DE 10 2014 220 791.6, filed in the Federal Republic of Germany on Oct. 14, 2014, the content of each of which is incorporated herein by reference in its entirety.

FIELD OF THE INVENTION

The present invention relates to a sensor for determining a concentration of particles in a gas flow, in particular of soot particles in the exhaust gas of an internal combustion engine.

BACKGROUND

Sensors which are used for determining the concentration of soot particles in an exhaust system of an internal combustion engine, in particular for monitoring diesel particulate filters, are known from the related art. For example, DE 10 2006 032 741 A1 and DE 10 2006 029 215 A1 each describes a particle sensor which has a carrier element and a sensor element, which is situated on a surface of the carrier element and may be exposed to the gas flow. The carrier includes in this case an electrically nonconductive, highly-insulating material, in particular a ceramic made of aluminum oxide. The sensor element situated on the surface of the carrier element has in this case an electrode structure made up of at least two measuring electrodes of different polarity, the measuring electrodes being designed in the form of an interdigital comb structure having individual finger electrodes, which are electrically connected to one another. The term "interdigital comb structure" arises from the fact that the finger electrodes of the two measuring electrodes mesh alternately like a comb. Each of the measuring electrodes designed in this way is connected via a strip conductor to a terminal contact for connection to a measuring and control unit. The interdigital comb structure is used as a resistance measuring structure, which is directly exposed to the gas flow during operation. If electrically conductive particles which are entrained in the gas flow, in particular soot particles having this property, accumulate on the sensor element, the electrical resistance thus changes between the two measuring electrodes. For example, the electrical resistance decreases with increasing particle concentration on the sensor element. The concentration of the accumulated particles may be determined from a change over time of the particular measured variable, in particular the electrical resistance, with the aid of the measuring and control unit, and the particle concentration in the gas flow may be inferred therefrom.

While typical particle sensors have an interdigital comb structure including finger electrodes, the finger electrodes having mutual distances in relation to one another which are equidistant, DE 10 2004 059 650 A1 describes a sensor for determining the concentration of particles in a gas flow in which the interdigital comb structure has a varying distance between the finger electrodes. In this way, a first area having finger electrodes situated far apart from one another and a second area having finger electrodes located closely adjacent to one another may be achieved. While the sensor element which has an interdigital comb structure including finger electrodes situated equidistantly in relation to one another forms a symmetrical electrical field upon application of a voltage between the measuring electrodes, which is characterized in that the electrical field has a consistent direction and strength between the finger electrodes, in the sensor element according to DE 10 2004 059 650 A1, a not spatially constant electrical field forms upon application of a voltage. Particles which are deposited between finger electrodes located closely adjacent to one another may form a conductive path rapidly in this area and may trigger a measuring signal in this way, whereby the sensitivity of the sensor increases. Conductive paths are also formed between finger electrodes situated far apart from one another by a successive accumulation of further particles, whereby a stronger signal increase is achieved over a longer period of time, which is higher than in the case of measuring electrodes situated equidistantly in relation to one another, which may finally result in an amplification of the sensor signal. In addition, the particle accumulation rate may be increased by amplified field gradients, which are generated in that the finger electrodes have a substructure, for example, in the form of regularly situated points, squares, dots, or other geometric shapes.

The sensor thus described is typically at least partially enclosed by at least one protective tube, which is used in particular for the flow supply of the gas flow along the sensor element. In general, the protective tube is designed to be chimney-shaped in this case, so that the gas flow is guided from an entry opening along the surface of the sensor element in the direction of an exit opening. In this way, the protective tube is to cause a preferably uniform flow over the sensor element along the main electrode direction, which is also referred to hereafter as the X direction, with preferably little angle dependence at the same time. As a result of this uniform, laminar flow over the sensor element by the gas flow, many particles do reach the vicinity of the sensor element, but, as present studies have shown, only a small fraction thereof actually accumulates on the surface of the sensor element. Only particles which flow in a layer close to the surface of the interdigital comb structure experience sufficiently strong attractive forces perpendicularly in relation to the main flow and are accelerated in this way in the direction of the sensor element, which is referred to hereafter as the Z direction, where they successively form electrically conductive particle paths, in particular soot paths, by corresponding accumulation.

In particle sensors according to the related art, only particles which are located in a layer having a distance above the electrode structure of typically significantly less than 500 μm experience a corresponding attraction due to the electrical field formed with the aid of the measuring electrodes. All particles which are located at a greater distance from the electrode structure, in contrast, are guided past the sensor element and leave the protective tube through the exit opening, without contributing to a measurable effect.

In contrast, particles which reach the catchment area of the attracting electrical field generally experience a quick timed acceleration, whereby the application to the electrode structure predominantly takes place in that region on the sensor element over which the gas flow flows over first. In this way, in many cases only a fraction of the existing surface area of the electrode structure on the sensor element is used to obtain a measurable signal, so that the sensor frequently only has a comparatively low sensitivity.

SUMMARY

An object of the present invention is to provide a sensor for determining a concentration of particles in a gas flow, in particular soot particles in the exhaust gas of an internal combustion engine, which has a preferably high sensitivity, without causing excessively early saturation of the sensor. This object is achieved in that, by way of a preferably optimal design of the electrode structure of the sensor element, the surface area of the electrode structure available on the sensor element may advantageously be used completely for the signal formation in the sensor while maintaining its dynamics.

For this purpose, the sensor for determining the concentration of particles in a gas flow includes at least one carrier element and at least one sensor element, which is situated on a surface of the carrier element and may be exposed to the gas flow. The sensor is in this case, as described above, in a preferred design, enclosed by at least one protective tube, which at least partially encloses the sensor and which is used in particular for supplying the gas flow over the sensor element. A sufficiently mechanically stable substrate is preferably used as the carrier element, which is advantageously made of a well-insulating material, in particular a ceramic, such as aluminum oxide.

The sensor element which may be exposed to the gas flow includes at least one electrode structure, the electrode structure including at least two measuring electrodes, the measuring electrodes having different polarities from one another. According to the present invention, the measuring electrodes are designed in this case in the form of an interdigital comb structure, which includes finger electrodes, which provides a resistance measuring structure in this way. As already defined at the outset, the term "interdigital comb structure" is understood as an electrode structure in which the finger electrodes of both measuring electrodes mesh alternately like a comb.

To achieve the above-mentioned object, the finger electrodes in the interdigital comb structure have mutual distances in relation to one another which are not equidistant over the entire electrode structure. Equidistant distances are understood as a design of the electrode structure in which finger electrodes have the same distance within the scope of the typical tolerances. In this way, it is to be ensured in particular that the electrical field which is generated between the finger electrodes when a voltage is applied to the measuring electrodes has a preferably homogeneous structure. Since, as has been established in studies and as was already described above, however, it is advantageous for the electrode structure to generate an inhomogeneous electrical field in the present sensor element, for this purpose, as indicated in DE 10 2004 059 650 A1, according to the present invention, the mutual distances of the finger electrodes are not selected to be equidistant over the entire electrode structure.

According to the present invention, the interdigital comb structure including the finger electrodes is designed in such a way that preferably over the entire length and entire width of the electrode structure, all areas which have a lesser distance of the finger electrodes in relation to a mean distance may also be used for the signal formation in the present sensor, whereby the sensitivity of the sensor may be significantly increased. For this purpose, according to the present invention, the proportion of the particles applied to the sensor element which may contribute to the signal formation is increased. On the other hand, however, sufficient areas which have a greater distance of the finger electrodes in relation to a mean distance are also to be provided in the interdigital comb structure, to ensure in this way the attraction of particles from more distant layers above the sensor element, which then accumulate in the following area having a shorter distance and in this way additionally contribute to the signal formation and avoid excessively early saturation while maintaining the dynamics of the sensor.

According to the present invention, this desired effect is achieved in that first areas having first, large distances of the finger electrodes and second areas having second, short distances of the finger electrodes are provided in the interdigital comb structure, the first distances exceeding the second distances, the first areas and the second areas on the interdigital structure at least partially each alternately adjoining one another. For example, the first, large distances differ from the second, short distances in that the first distances are greater than a mean distance, while the second distances are less than the mean distance, the mean distance being able to correspond to a mean value or median of the distances between the finger electrodes in the X and/or Y directions, the mean distance being able to be determined from all distances which are used or from extreme values, i.e., the greatest distance and the least distance in the electrode structure.

The first areas, which have the first, large distances, are essentially used according to the present invention as electrostatic collectors having a greater extensive effect of the electrical field in comparison to the related art. The particles which are thus detected and attracted from greater distances by the sensor element preferably accumulate on the second areas having the second, short distances, in particular those second areas which each directly adjoin the first areas, and may form paths thereon. In this way, the signal formation may essentially only take place within the second areas. According to example embodiments of the present invention, the first areas and the second areas are situated at least partially alternating on the surface of the sensor element, preferably over broad regions on the surface of the sensor element, thereby contributing to promoting an accumulation of particles from the gas flow which passes over the sensor element.

The second areas preferably have the same, optimal short electrode distance, which is ascertained with the aid of numerical calculations, while the electrode distances in the first areas preferably change in steps, a change taking place in particular in the flow direction (X direction). Therefore, on the one hand, preferably many of the particles which are conducted in the gas flow over the sensor element accumulate on the sensor element, on which they may produce a conductive path as a result of their intrinsic electrical conductivity, as soon as sufficient particles have accumulated at a point between the finger electrodes without, on the other hand, an excessively early saturation of the sensor taking place in only one partial area of the electrode surface as a result of a local accumulation, as in the related art. In this way, the object according to the present invention of increasing the sensitivity of the present sensor is fulfilled without restricting its dynamics.

In one preferred embodiment, in both the first areas and in the second areas, the distances of the finger electrodes are selected in such a way that they either increase or decrease on the sensor element, viewed in the direction of the gas flow, in particular depending on the flow conditions, which are produced in particular by the design of the protective tube above the sensor element. In particular, this increase or decrease takes place quasi-continuously, which may also be referred to as stepped or in steps. This is understood as a change of the distances in which the distance remains constant or even increases over one region, to assume a lesser value in the adjoining region in the event of a decrease or a higher value in the event of an increase. Alternatively, as described above, only the distances in the first areas may increase or decrease in steps, while they remain constant in the second areas.

The reverse case, that the distances in the second areas increase or decrease in steps, while they remain constant in the first areas, may also be advantageous. In this further embodiment, the mutual distances of the finger electrodes in the interdigital comb structure are established in such a way that they may either increase or decrease perpendicularly in relation to the direction of the gas flow, which is also referred to as the Y direction. It may also be advantageous in this embodiment that the change of the distances of the finger electrodes takes place in quasi-continuous or stepped form. Such a variation of the distances may also provide a contribution to increasing the sensitivity of the present sensor with an appropriate design.

In one particular embodiment, a surface area of the finger electrodes in the interdigital comb structure which extend perpendicularly in relation to the direction of the gas flow, i.e., in the Y direction, may be less than the surface area of the finger electrodes in the interdigital comb structure which extend in the direction of the gas flow, i.e., in the X direction. It has been shown in corresponding studies that electrode structures which have a preferably small proportion of finger electrodes which extend perpendicularly in relation to the flow direction, i.e., in the Y direction, can result in a greater utilization of the electrode surface area for accumulation of particles and therefore a formation of soot paths.

In another embodiment, a thickness which the finger electrodes have in the interdigital comb structure may vary over the interdigital comb structure on the sensor element. In this case, it may be advantageous in particular that the thickness of the finger electrodes increases or decreases in the direction of the gas flow, i.e., in the X direction. Depending on the flow conditions above the sensor element, either a lesser or a greater thickness of the finger electrodes on the parts of the interdigital comb structure which first come into contact with the gas flow may provide an additional contribution to increasing the sensitivity of the sensor. It may have a particularly advantageous effect with respect to an increase of the sensitivity of the present sensor if, in combination with the alternating electrode distances between the first areas and the second areas, in particular the finger electrodes of the first areas, which have greater distances in relation to one another, have a greater thickness.

In one preferred embodiment, the ratio of a first surface area, which the first areas occupy on the sensor element, in relation to a second surface area, which the second areas occupy on the sensor element, are in the interval from at least 0.1, preferably at least 0.3, particularly preferably at least 0.4, up to 0.9 inclusive, preferably up to 0.7 inclusive, particularly preferably up to 0.6 inclusive, the total of the two ratios being 1.0, the ratio of the two surface area components preferably being determined with the aid of numerical simulations.

In another embodiment, the finger electrodes, i.e., all finger electrodes, a part of the finger electrodes, or all finger electrodes of one area in the interdigital comb structure include additional substructures. Exemplary substructures can be inferred from the exemplary embodiments set forth in the following description or DE 10 2004 059 650 A1. With the aid of additional substructures, a further increase of the sensitivity of the present sensor may be achieved.

Known methods from thick-film technology from the related art can advantageously be used for manufacturing the sensor according to the present invention, in order to manufacture on this basis the electrode structure in the form of an interdigital comb structure including finger electrodes. Already known methods, for example, screen printing or stencil printing, are suitable for this purpose here. However, to further increase the sensitivity of the present sensor also by way of the selected manufacturing method, it is advantageous to use novel methods for fine structuring of the finger electrodes in the interdigital comb structure. As studies have shown, the electrode structure can preferably be formed in this case with the aid of laser structuring, in particular using a picosecond laser, which enables a rapid and flexible production of nearly any structure made of a conductive electrode paste applied to the carrier structure.

Alternatively or additionally, the electrode structures, in particular electrode structures which have preferably short distances of the finger electrodes, can be produced with the aid of a 3D printer. For this purpose, for example, reference is made to the article by M. Hermatschweiler, 3*D-Druck auf der Mikroskala erreicht neue Dimensionen* (3D printing at microscale achieves new dimensions), Sensormagazin, February 2013, pages 36-39, which provides an overview of the use of 3D printers from small-scale series production with the aid of rapid prototyping up to digital manufacturing in the automobile industry.

Preferred exemplary embodiments of the present invention are illustrated in the figures and will be explained in greater detail in the following description.

DETAILED DESCRIPTION

Figure 1:
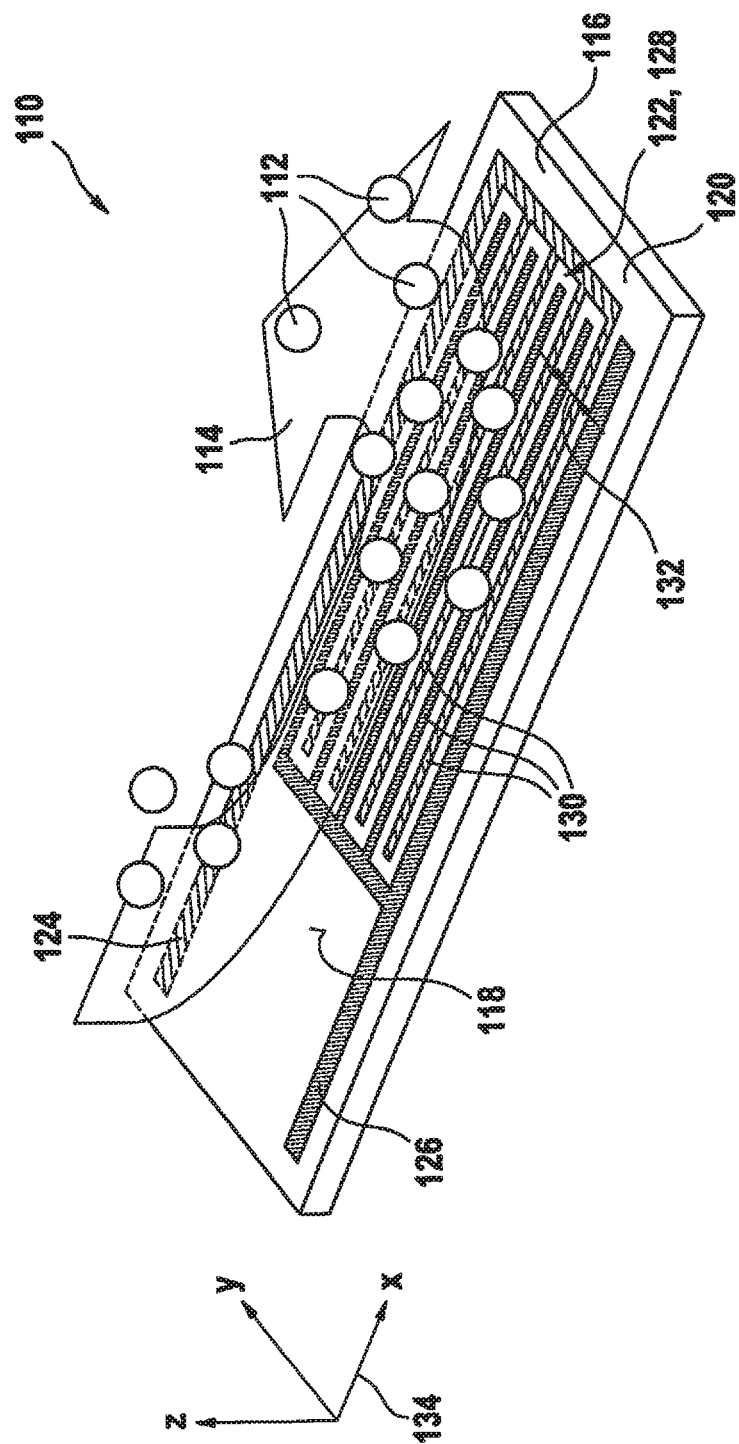
FIG. 1 shows a sensor known from the related art for determining a concentration of particles in a gas flow, according to an example embodiment of the present invention.

FIG. 1 schematically shows a conventional sensor 110 for determining a concentration of particles 112 in a gas flow 114, in particular soot particles in the exhaust gas of an internal combustion engine. Sensor 110 includes in this case a carrier element 116 and a sensor element 120, which is situated on surface 118 of carrier element 116 and can be exposed to gas flow 114. Sensor element 120 includes an electrode structure 122 made up of two measuring electrodes 124, 126, the two measuring electrodes 124, 126 having different polarities from one another. Designing measuring electrodes 124, 126 of electrode structure 122 in the form of an interdigital comb structure 128 including finger electrodes 130 is known from the related art. Finger electrodes 130 typically have mutual distances 132, which are generally equidistant. Electrode structure 122 on sensor element 120 forms a coordinate system 134 in this preferred embodiment, in which directions X, Y, and Z may be defined as follows: the X direction corresponds to the direction of gas flow 114 above sensor element 120; the Y direction is perpendicular to the direction of the gas flow in the plane of the electrode structure; and the Z direction is perpendicular to surface 118 of sensor element 120, which includes electrode structure 122 in the form of interdigital comb structure 128. Coordinate system 124 is also used in this form in the following drawings.

Figure 2A:
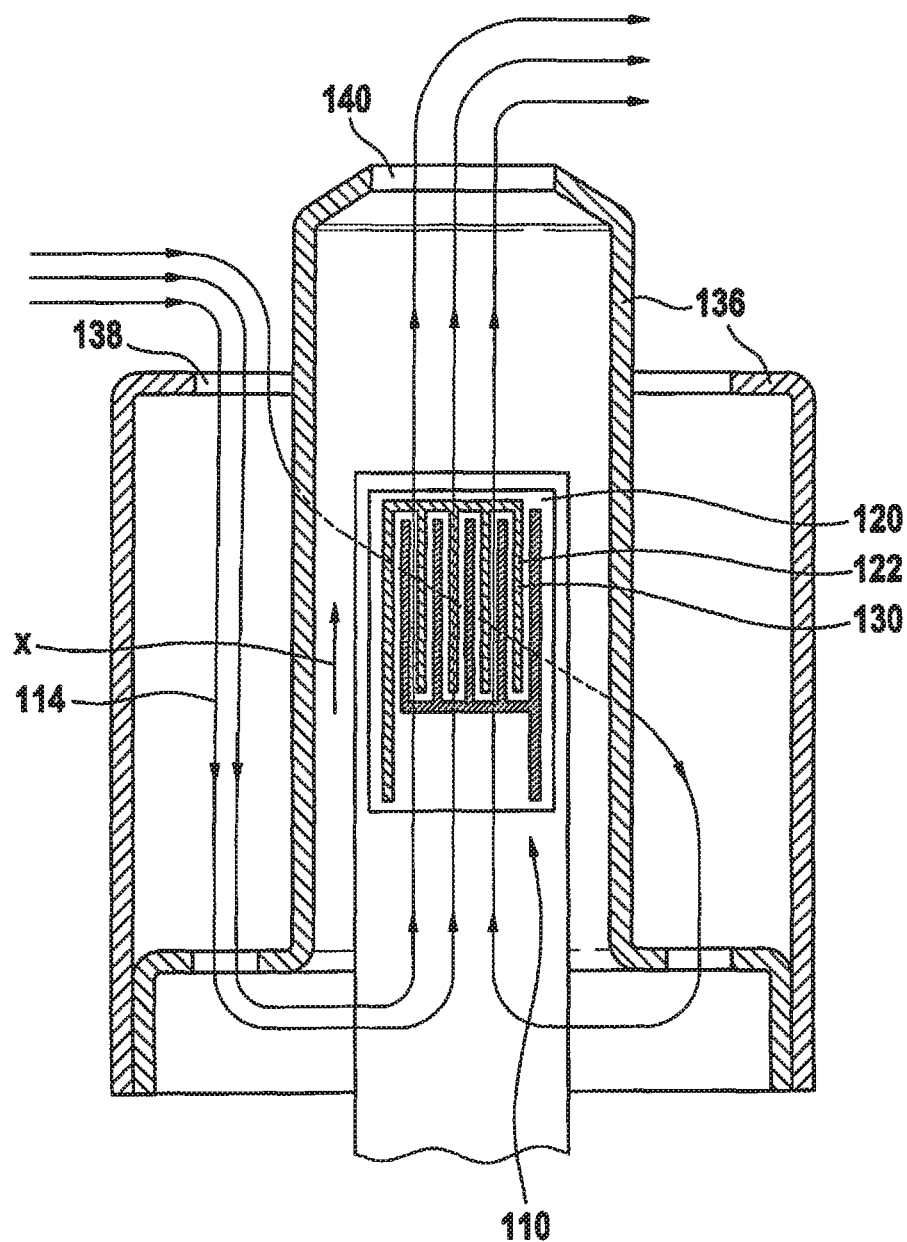
FIGS. 2*a*-2*c* show a schematic representation of a conventional introduction of the sensor into a protective housing and the associated guiding of the gas flow in vertical section.
Figure 2B:
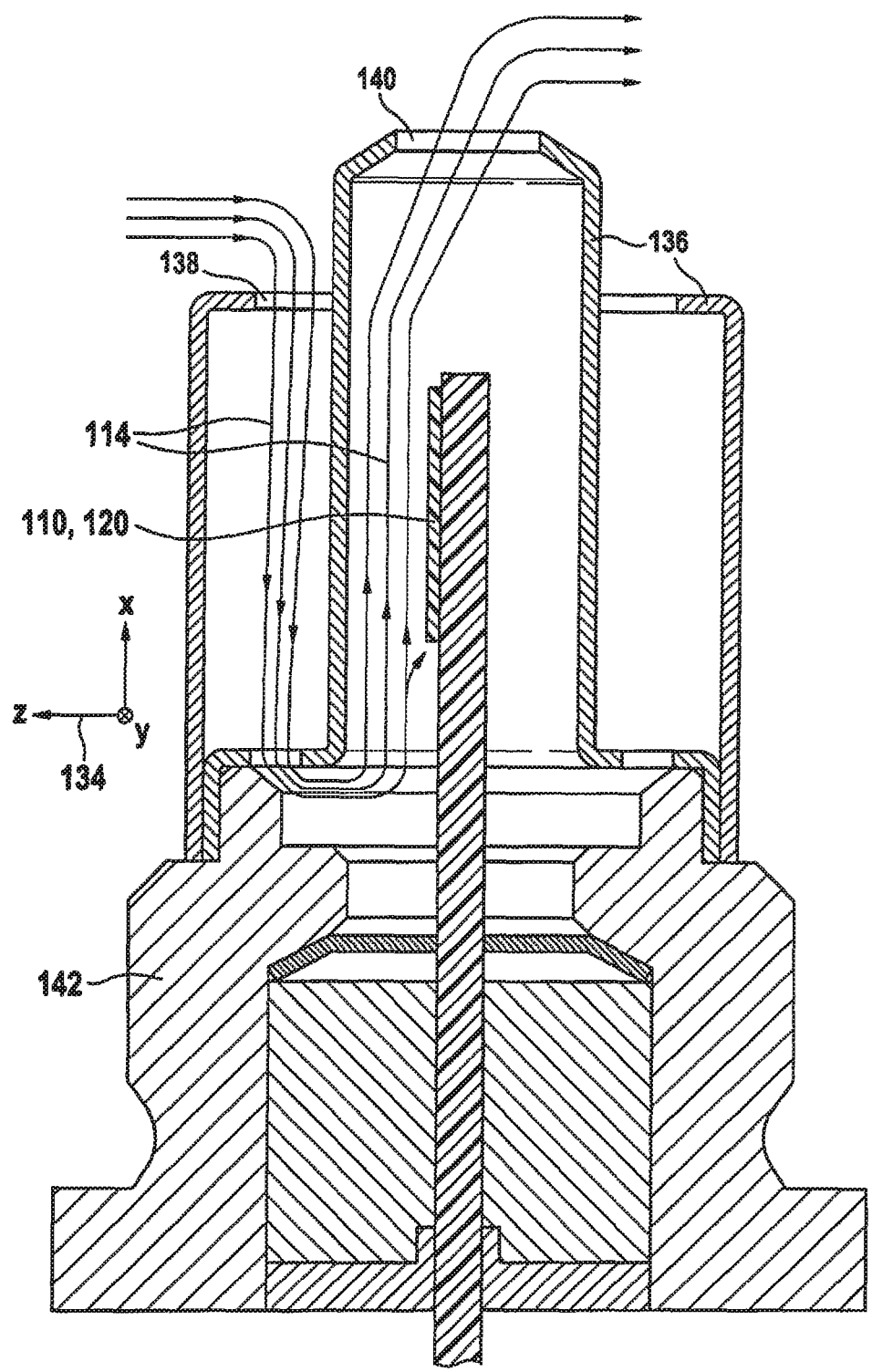
Figure 2C:
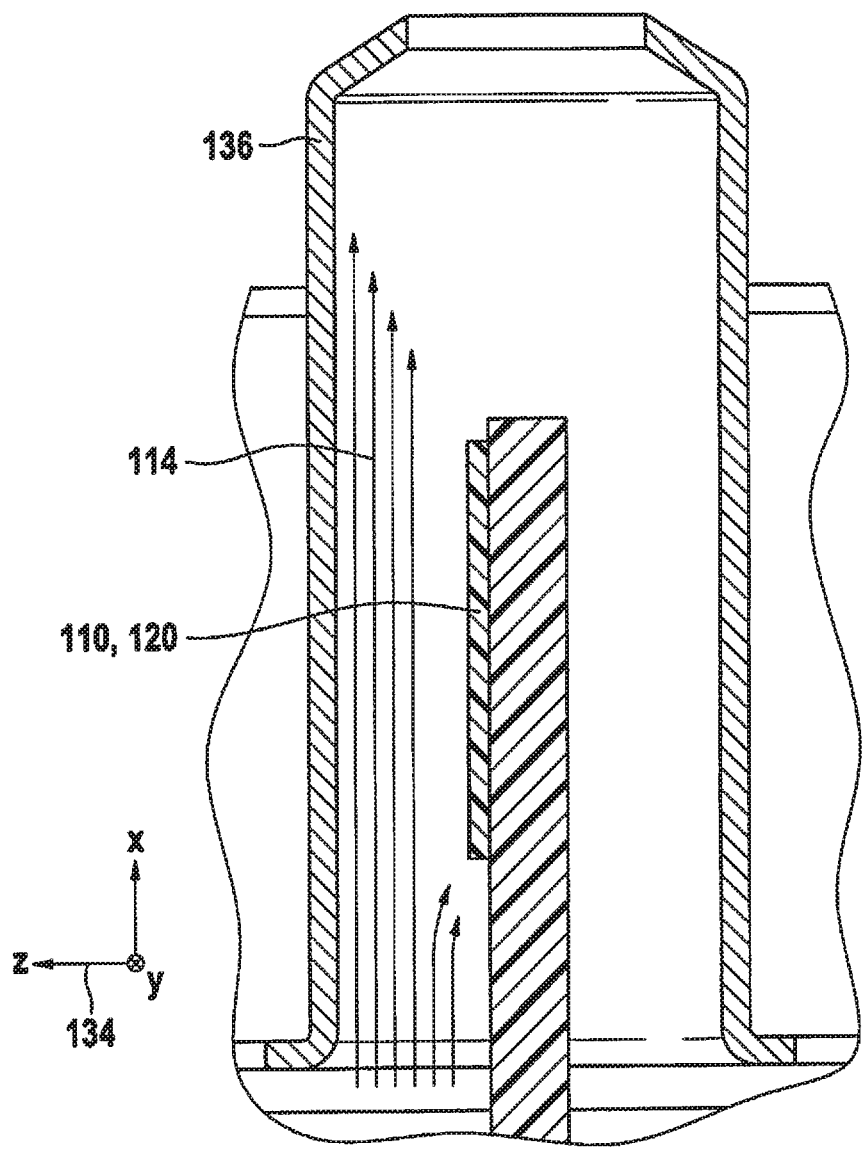

FIG. 2a-2c schematically show a perpendicular section through a protective housing 136, which encloses sensor 110. Protective housing 136 has an entry opening 138, through which gas flow 114 can enter the interior of protective housing 136. Protective housing 136 is designed in such a way that gas flow 114 is preferably guided in parallel, i.e., in the X direction, over sensor 110, in particular over electrode structure 122 on sensor element 120, before gas flow 114 leaves the interior of protective housing 136 through exit opening 140.

FIG. 2a schematically shows for this purpose the flow guiding of gas flow 114 through protective housing 136, sensor element 120 being shown in transversal section. Electrode structure 122 on the sensor element is aligned in this case in such a way that finger electrodes 130 extend in parallel to the direction of the flow of gas flow 114, i.e., in the X direction.

FIGS. 2b and 2c show a lateral sectional image of protective housing 136, in which sensor element 120 is exposed to gas flow 114, attached to a hexagon 142, FIG. 2c showing a detail from FIG. 2b including incorporated coordinate system 134.

Figure 3A:
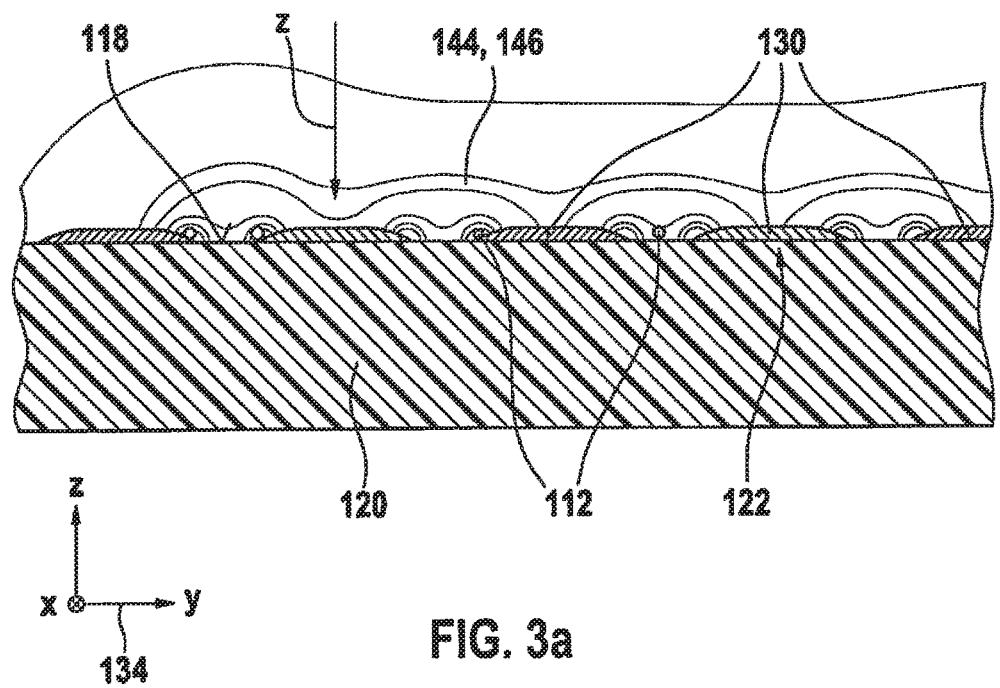
FIG. 3*a* shows a schematic representation in cross section of a conventional electrical field generated by an electrode structure on the sensor element.

FIG. 3a shows electrical field 144, which is generated by electrode structure 122 of sensor element 120, in the form of a cross section. Only particles which arrive in a layer 136 close to surface 118 of electrode structure 122 experience a sufficiently strong attractive force in the Z direction and may form soot paths between finger electrodes 130 in this way.

Figure 3B:
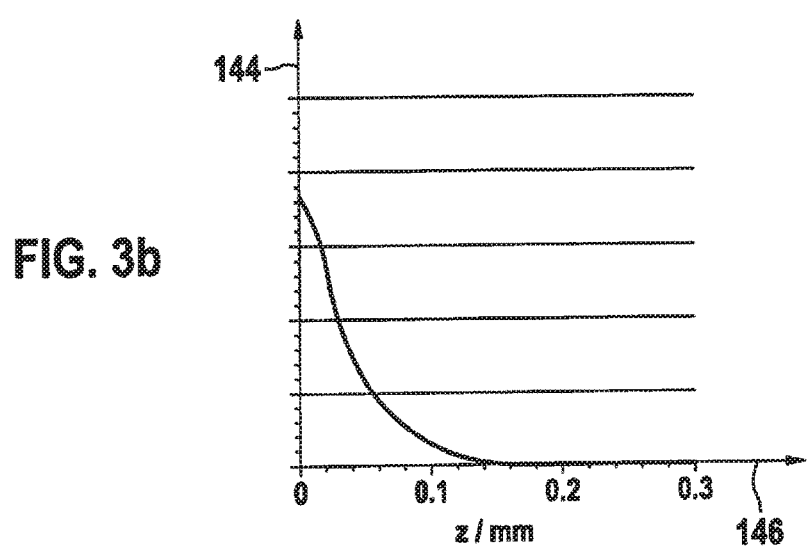
FIG. 3*b* shows an effect of an electrical field in a conventional sensor.
Figure 4:
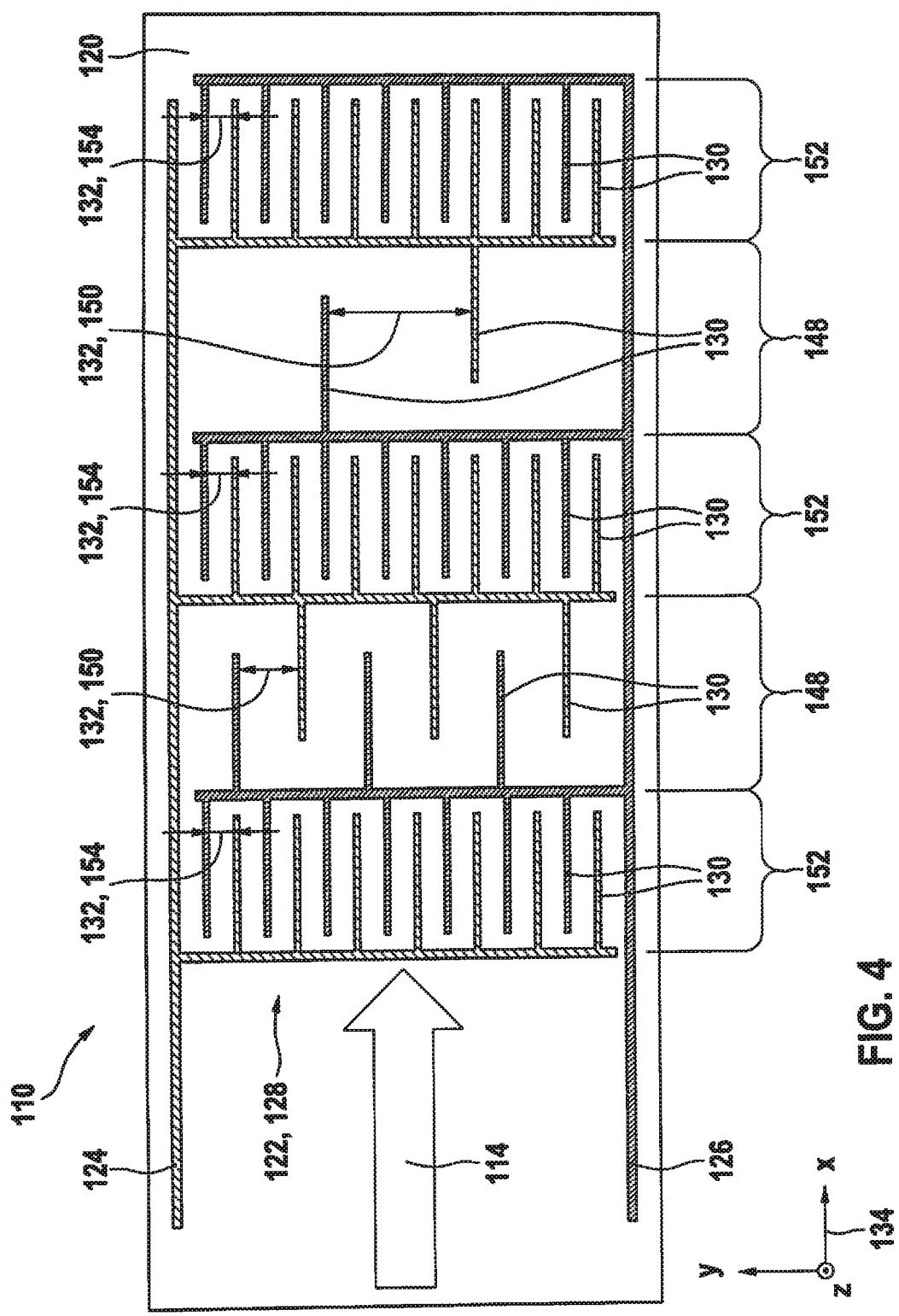
FIGS. 4-7 show schematic representations in top view of electrode structures, according to example embodiments of the present invention.
Figure 5:
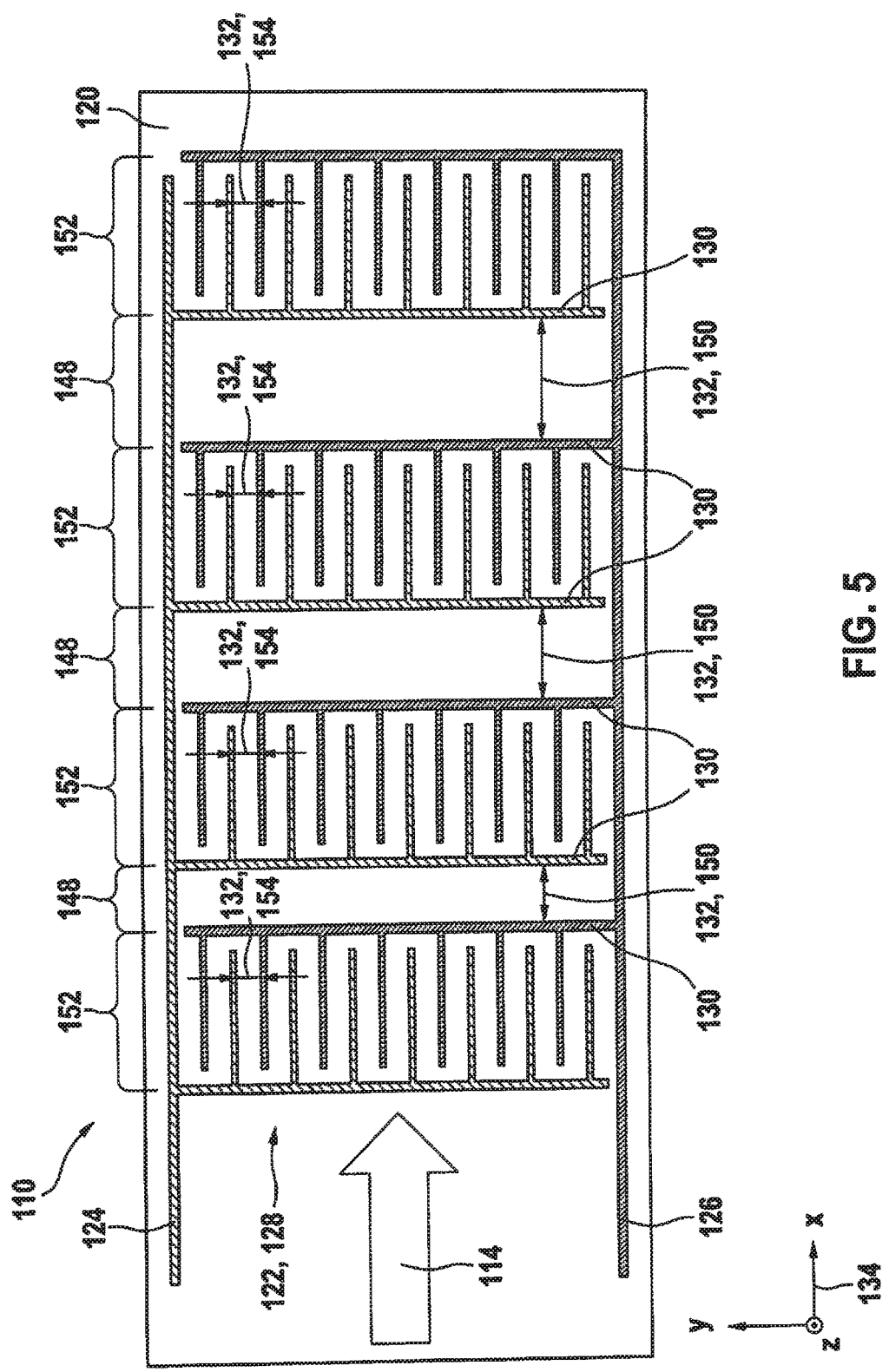
Figure 6:
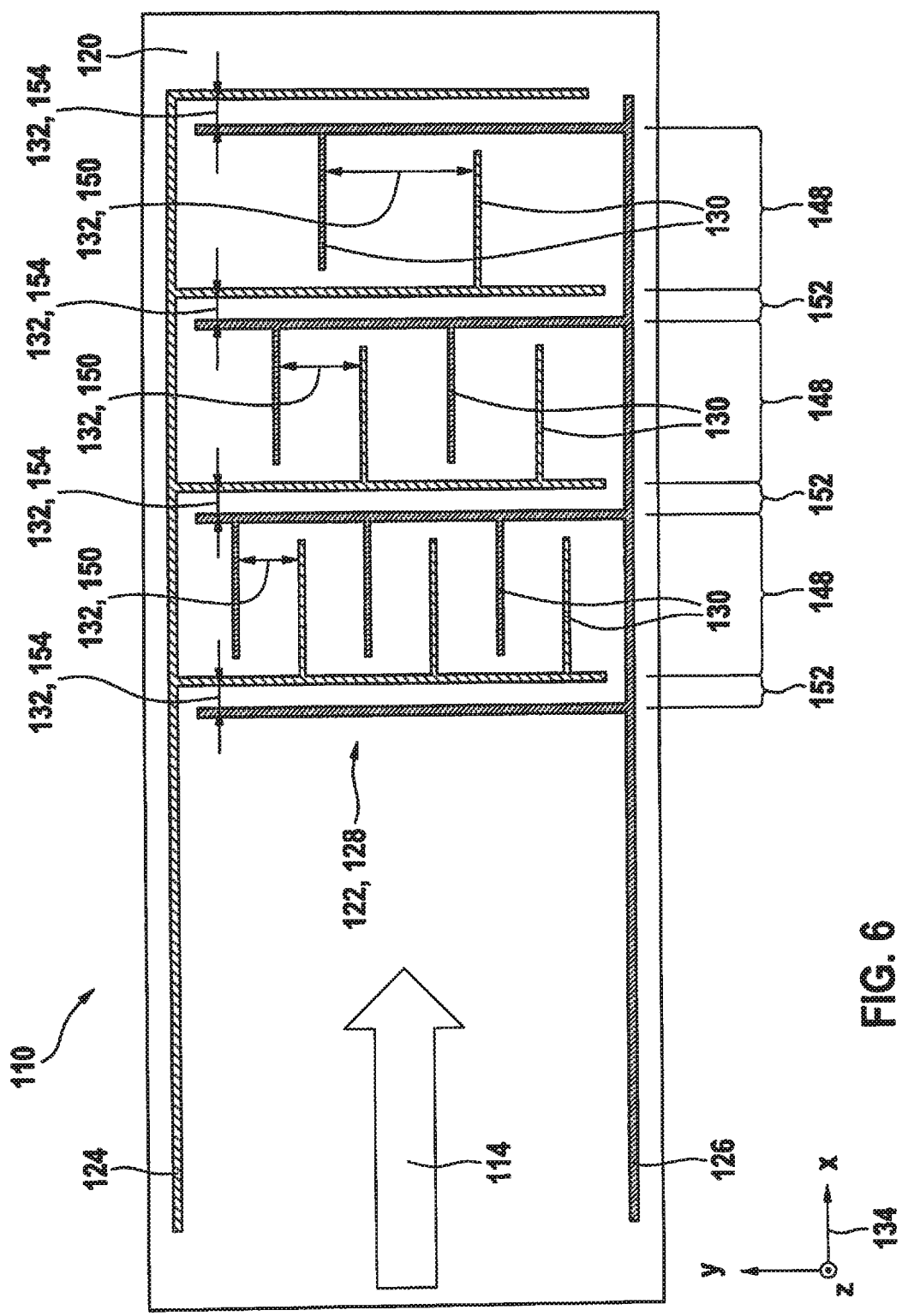
Figure 7:
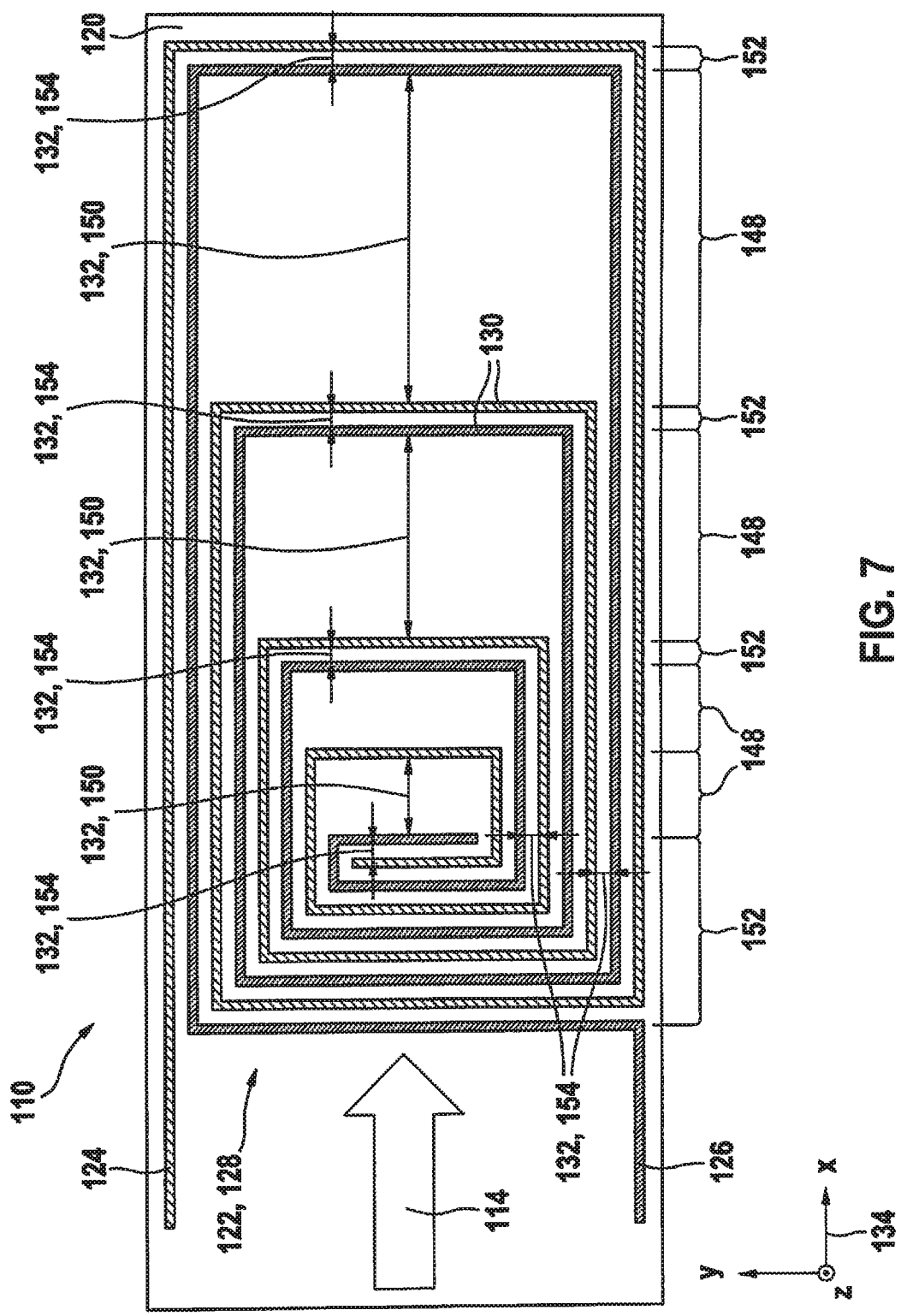

FIG. 3b shows that in a sensor 110, which is known from the related art, electrical field 144 may solely exert an effect on the particles in the gas flow within a layer 146, which are located within a layer 146 above surface 118 of electrode structure 112, whose thickness has a value of typically significantly less than 0.5 mm.

FIGS. 4-12 show a sensor 110 according to example embodiments of the present invention. Therein, sensor element 120 includes above-described electrode structure 122 in the form of interdigital comb structure 128 including finger electrodes 130, distances 132 of finger electrodes 130 not being equidistant in relation to one another over entire electrode structure 122.

According to an example embodiment of the present invention, interdigital comb structure 128 includes first areas 148 having first, greater distances 132, 150 of finger electrodes 130 and second areas 152 having second, shorter distances 132, 154 of the finger electrodes, first distances 132, 150 exceeding second distances 132, 154. First, greater distances 132, 150 differ from second, shorter distances 132, 154 in this case in that first, greater distances 132, 150 are greater than a mean distance, while second, shorter distances 132, 154 are less than the mean distance, the mean distance being able to correspond to a mean value or median of the distances between finger electrodes 130 in the X and/or Y directions, the mean distance being able to be determined from all distances used or from extreme values, i.e., the greatest distance and the smallest distance in electrode structure 122.

According to an example embodiment of the present invention, in this case first areas 148 and second areas 152 in interdigital comb structure 128 each alternately adjoins one another at least over large regions on surface 118 of sensor element 120, i.e., first area 148 having first, greater distances 132, 150 of finger electrodes 130 in relation to one another is followed by second area 152 having second, shorter distances 132, 154 of finger electrodes 130 in relation to one another, whereupon, as long as space is still present on surface 118 of sensor element 120, further first area 148 having first, greater distances 132, 150 of finger electrodes 130 in relation to one another is situated.

Possible embodiments of interdigital comb structure 128 according to the present invention are deducible from the specific embodiments shown in FIGS. 4-12. Exemplary embodiments are shown therein, in which the length of finger electrodes 130 in interdigital comb structure 128, which extend perpendicularly in relation to the direction of gas flow 114, is less than the length of finger electrodes 114 which extend in the direction of gas flow 114. Further embodiments, which can also be a combination of the illustrated embodiments or can have further elements (not shown here), are also conceivable, however.

Figure 8:
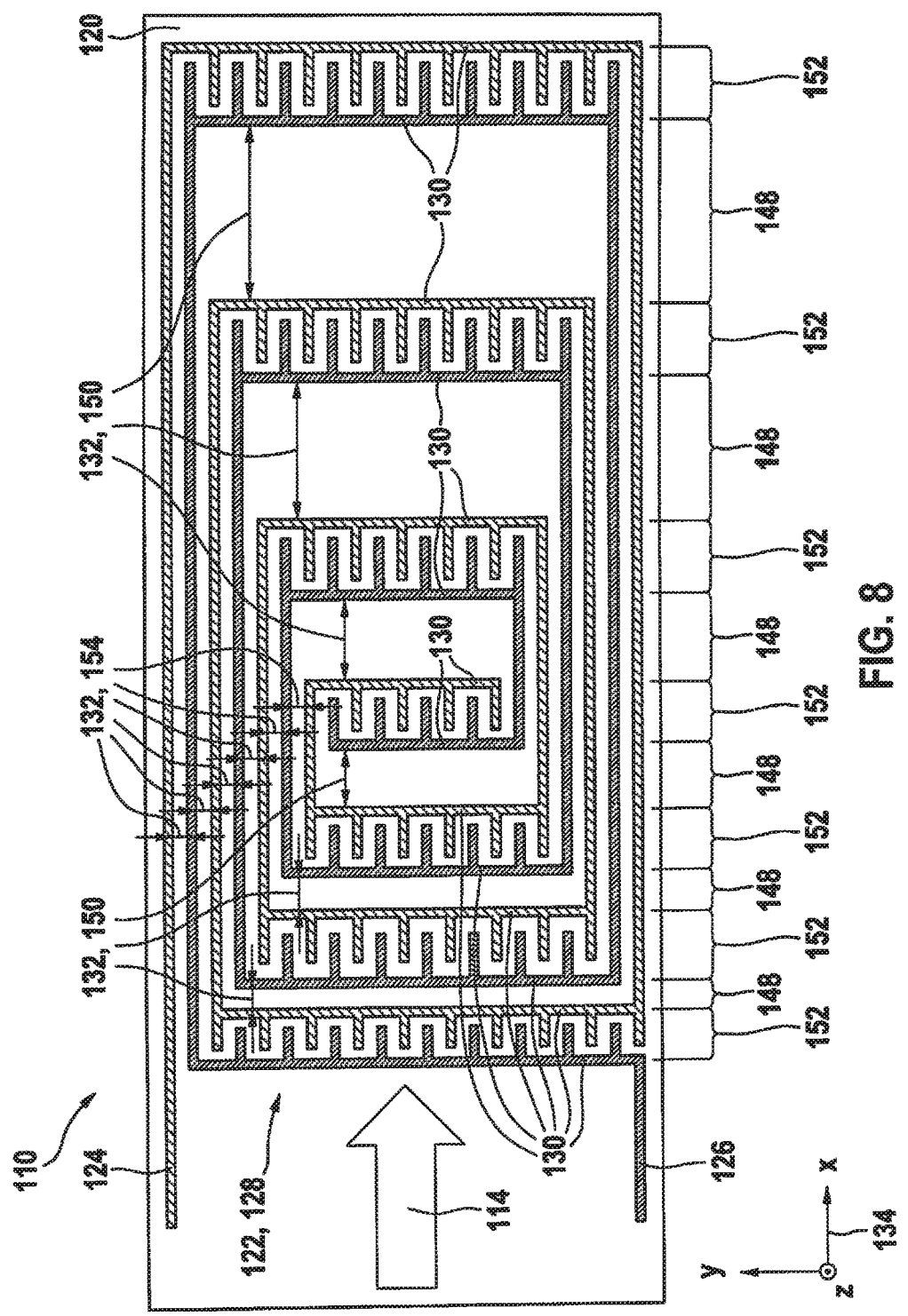
FIG. 8 shows a schematic representation in top view of the electrode structure, with additional substructures, according to another example embodiment of the present invention.
Figure 9:
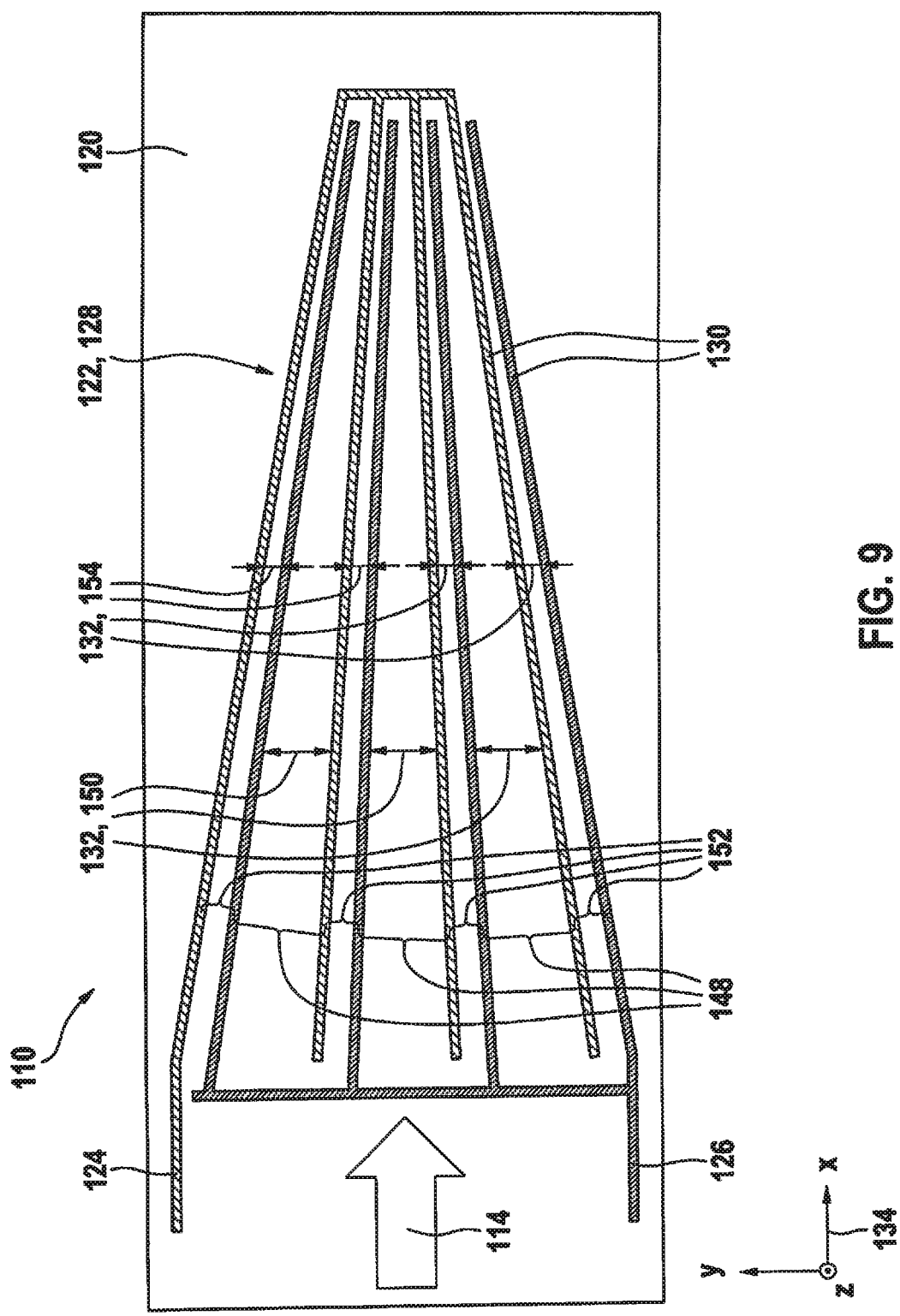
FIGS. 9-10 show schematic representations in top view of electrode structures, in trapezoidal form, according to example embodiments of the present invention.
Figure 10:
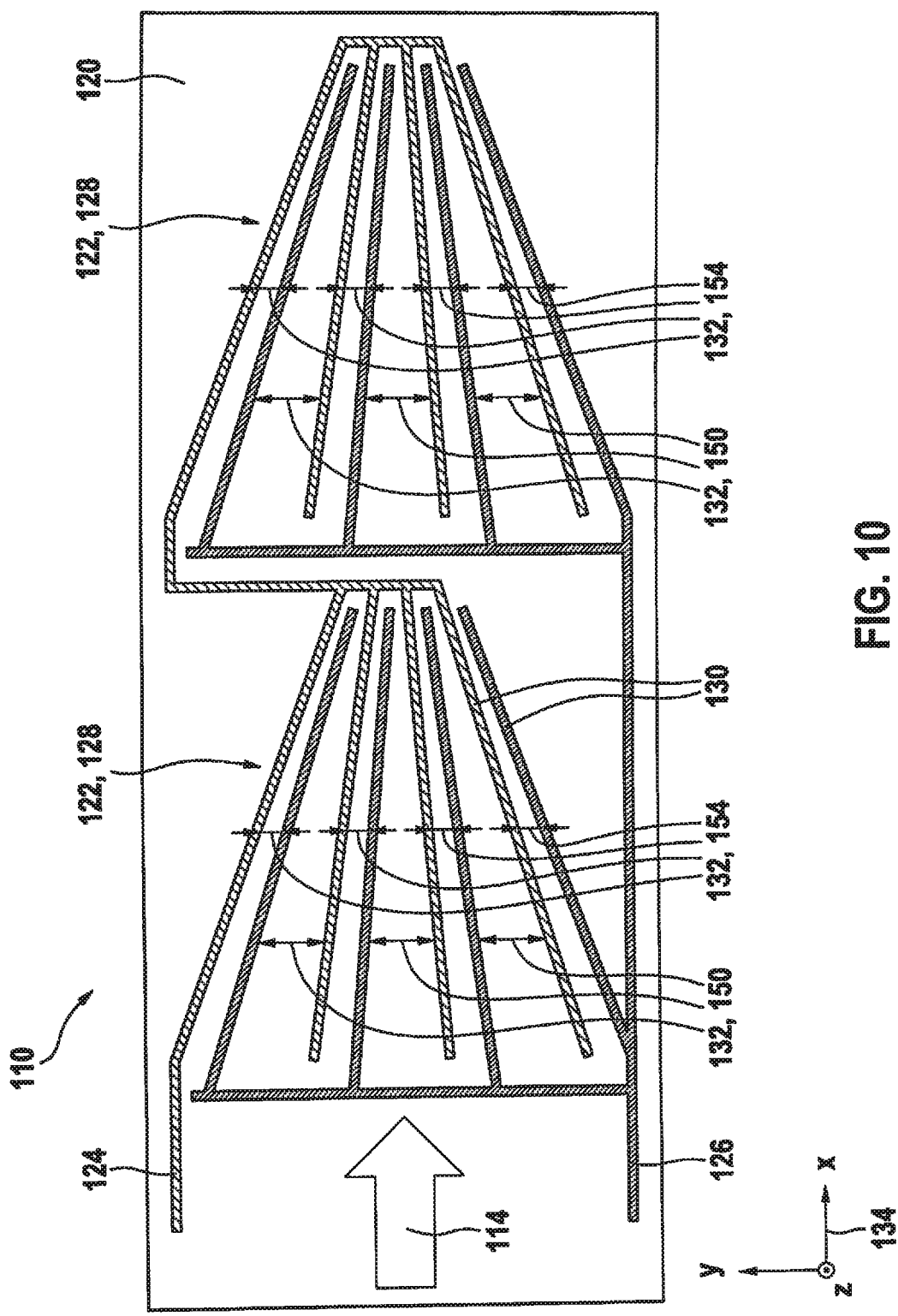

FIGS. 4-8 show example embodiments in which distances 132 of finger electrodes 130 in interdigital comb structure 128 increase in steps in the direction of gas flow 114, while FIGS. 9-10 illustrate example embodiments in which distances 132 of finger electrodes 130 in interdigital comb structure 128 decrease continuously in the direction of gas flow 114 as a result of their trapezoidal arrangement. Combinations of these embodiments, for example, uniform first distances 132, 150 of finger electrodes 130 in first areas 148 and uniform second distances 132, 154 of finger electrodes 130 in second areas 152 in spite of the trapezoidal arrangement of electrode structure 122 in interdigital comb structure 128 according to FIGS. 11 and 12, are also conceivable as further example embodiments.

Figure 11:
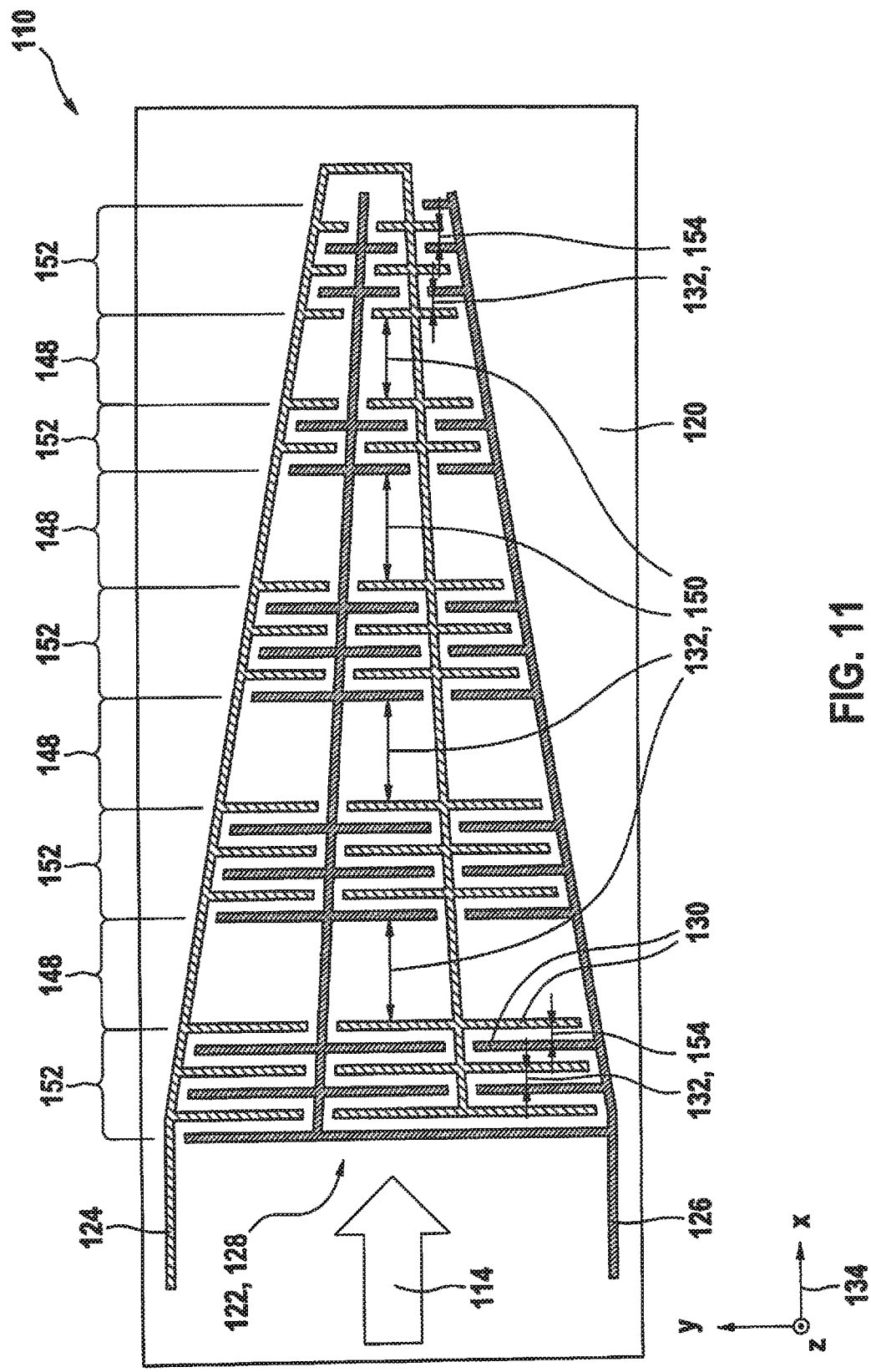
FIGS. 11 through 12 show schematic representations in top view of further embodiments of electrode structures according to the present invention in trapezoidal form, which include additional substructures.
Figure 12:
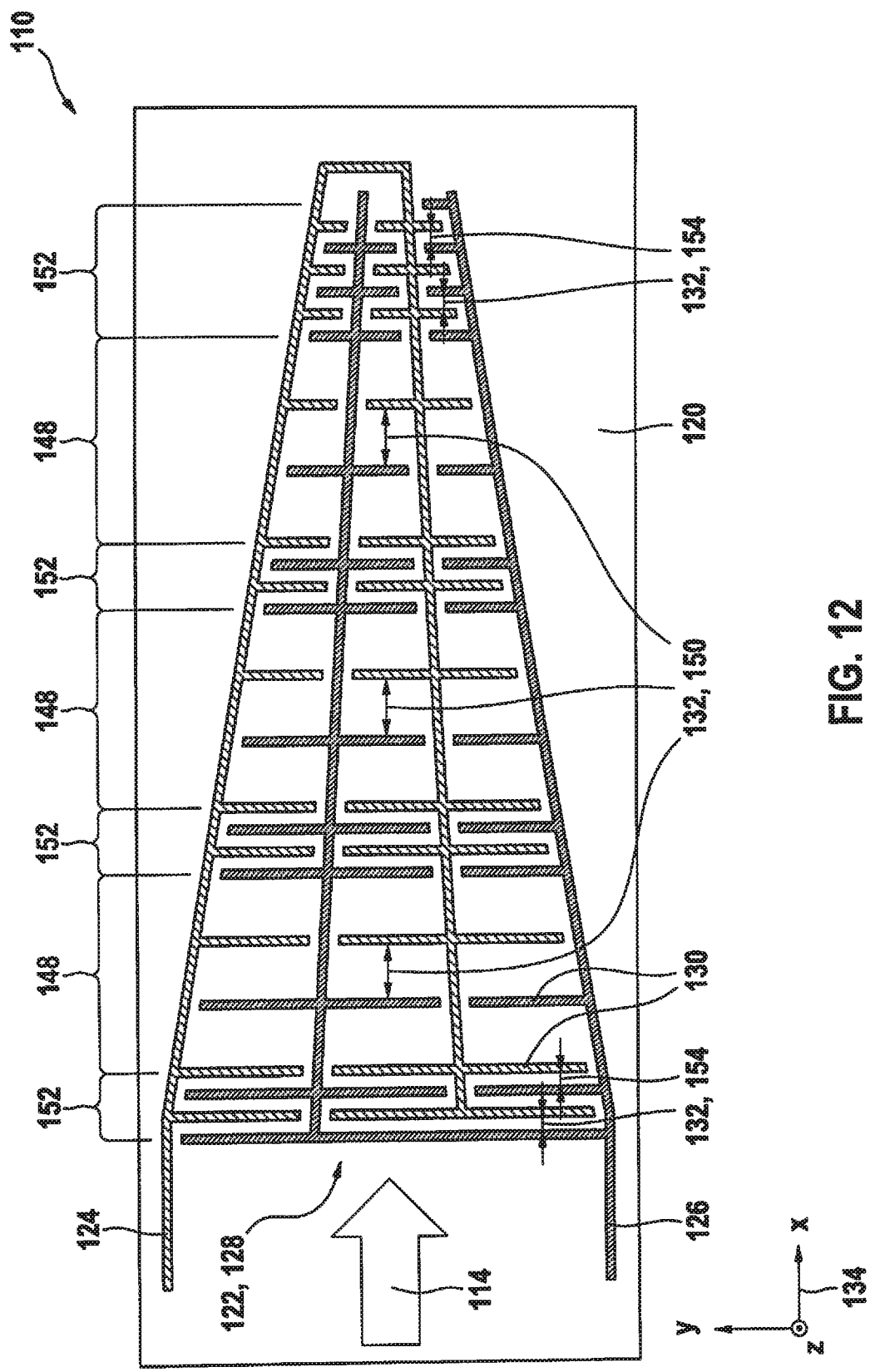

In addition, as shown by way of example in FIGS. 8, 11, and 12, finger electrodes 130 in interdigital comb structure 128 can include substructures which, in particular with a suitable arrangement, are capable of further increasing the sensitivity of sensor element 120.

What is claimed is:
1. A device for determining a concentration of particles in a gas flow, the device comprising:
  a carrier; and
  a sensor that is situated on a surface of the carrier and that includes an electrode structure that includes at least two measuring electrodes;
  wherein:
    the device is configured for exposure of the sensor to the gas flow;
    the at least two measuring electrodes are of different polarities and are formed as an interdigital comb structure that includes finger electrodes;
    the finger electrodes are distributed in first areas and in second areas;

with respect to respective pairs of immediately adjacent ones of the finger electrodes in the first areas, the finger electrodes of the respective pair are at a first distance from each other;

with respect to respective pairs of immediately adjacent ones of the finger electrodes in the second areas, the finger electrodes of the respective pair are at a second distance from each other;

the first distance exceeds the second distance; and the first areas and the second areas at least partially adjoin each other alternately, wherein the finger electrodes in the first areas and the finger electrodes in the second areas have a same width, wherein the second areas having a lesser distance of the finger electrodes in relation to a mean distance is used for signal formation in the present sensor, so as to increase a sensitivity of the sensor, and wherein the first areas having a greater distance of the finger electrodes in relation to a mean distance is provided in the interdigital comb structure, to provide for an attraction of particles from more distant layers above the sensor element, which then accumulate in the second areas having the lesser distance so as to contribute to the signal formation and avoid early saturation of the sensor, wherein the first areas and the second areas in the interdigital comb structure each alternately adjoin one another at least over regions on a surface of the sensor element, wherein the mean distance corresponds to a mean value or median of distances between the finger electrodes in a Y direction, and wherein the mean distance is determined from all distances used or from extreme values, including a greatest distance and a smallest distance in the electrode structure, and wherein the Y-direction is generally perpendicular to a direction of the gas flow in the plane of the electrode structure, and wherein a X-direction is generally parallel to the direction of the gas flow above the sensor element, and wherein a Z-direction is perpendicular to a surface of the sensor element and to the X-direction and the Y-direction.

2. The sensor of claim 1, wherein at least one of the first distance and the second distance increases in a direction of the gas flow on the surface of the sensor.

3. The sensor of claim 1, wherein at least one of the first distance and the second distance increases perpendicularly to a direction of the gas flow on the surface of the sensor.

4. The sensor of claim 1, wherein at least one of the first distance and the second distance decreases in a direction of the gas flow on the surface of the sensor.

5. The sensor of claim 1, wherein at least one of the first distance and the second distance decreases perpendicularly to a direction of the gas flow on the surface of the sensor.

6. The sensor of claim 1, wherein at least one of the first distance and the second distance gradually increases or decreases.

7. The sensor of claim 1, wherein the finger electrodes extend both perpendicularly to a direction of the gas flow and in the direction of the gas flow, and a length of the extension perpendicularly to the direction of the gas flow is less than the length of the extension in the direction of the gas flow.

8. The sensor of claim 1, wherein a thickness of the finger electrodes varies over the interdigital comb structure.

9. The sensor of claim 8, wherein, in at least one of (a) the first areas and (b) the second areas, the thickness increases in a direction of the gas flow on the surface of the sensor.

10. The sensor of claim 8, wherein, in at least one of (a) the first areas and (b) the second areas, the thickness increases perpendicularly to a direction of the gas flow on the surface of the sensor.

11. The sensor of claim 8, wherein, in at least one of (a) the first areas and (b) the second areas, the thickness decreases in a direction of the gas flow on the surface of the sensor.

12. The sensor of claim 8, wherein, in at least one of (a) the first areas and (b) the second areas, the thickness decreases perpendicularly to a direction of the gas flow on the surface of the sensor.

13. The sensor of claim 1, wherein a ratio of a first surface area, which the first areas occupy on the sensor, to a second surface area, which the second areas occupy on the sensor, is between at least 0.1 to at most 0.9.

14. The sensor of claim 1, wherein the finger electrodes include substructures.

15. The sensor of claim 1, wherein the particles whose concentration the device is configured to determine are soot particles in an exhaust gas of an internal combustion engine.

16. A method for providing a device for determining a concentration of particles in a gas flow, the method comprising:
providing a carrier; and
providing a sensor on a surface of the carrier;
wherein:
the sensor includes an electrode structure that includes at least two measuring electrodes;
the at least two measuring electrodes are of different polarities and are formed as an interdigital comb structure that includes finger electrodes;
the providing of the sensor includes forming the interdigital comb structure on the surface of the carrier using at least one of laser structuring and a 3D printer;
the finger electrodes are distributed in first areas and in second areas;
with respect to respective pairs of immediately adjacent ones of the finger electrodes in the first areas, the finger electrodes of the respective pair are at a first distance from each other;
with respect to respective pairs of immediately adjacent ones of the finger electrodes in the second areas, the finger electrodes of the respective pair are at a second distance from each other;
the first distance exceeds the second distance; and
the first areas and the second areas at least partially adjoin each other alternately,
wherein the finger electrodes in the first areas and the finger electrodes in the second areas have a same width, and
wherein the second areas having a lesser distance of the finger electrodes in relation to a mean distance is used for signal formation in the present sensor, so as to increase a sensitivity of the sensor, and wherein the first areas having a greater distance of the finger electrodes in relation to a mean distance is provided in the interdigital comb structure, to provide for an attraction of particles from more distant layers above the sensor element, which then accumulate in the second areas having the lesser distance so as to contribute to the signal formation and avoid early saturation of the sensor, wherein the mean distance corresponds to a mean value or median of distances between the finger electrodes in a Y direction, and wherein the mean distance is determined from all distances used or from extreme values, including a greatest distance and a smallest distance in the electrode structure, and wherein the Y-direction is generally perpendicular to a direction of the gas flow in the plane of the electrode structure, wherein a X-direction is generally parallel to the direction of the gas flow above the sensor element, and wherein a Z-direction is perpendicular to a surface of the sensor element and to the X-direction and the Y-direction.

\* \* \* \* \*